(12) United States Patent
Knaan et al.

(10) Patent No.: US 7,246,904 B2
(45) Date of Patent: Jul. 24, 2007

(54) LINE-OF-SIGHT DETECTION METHOD AND APPARATUS THEREFOR

(75) Inventors: Dotan Knaan, Jerusalem (IL); Jeremy Yermiyahu Kaminski, Jerusalem (IL); Adi Shavit, Jerusalem (IL); Dana Shavit, Jerusalem (IL); Kazufumi Suzuki, Tokyo (JP); Norio Ichihashi, Tokyo (JP); Akio Takahashi, Wako (JP); Akihito Kimata, Wako (JP)

(73) Assignee: Honda Motor Co., Ltd., Tokyo (JP)

( * ) Notice: Subject to any disclaimer, the term of this patent is extended or adjusted under 35 U.S.C. 154(b) by 250 days.

(21) Appl. No.: 11/078,144

(22) Filed: Mar. 11, 2005

(65) Prior Publication Data

US 2005/0200806 A1 Sep. 15, 2005

(30) Foreign Application Priority Data

Mar. 12, 2004 (JP) ............................ 2004-071256

(51) Int. Cl.
*A61B 3/14* (2006.01)
(52) U.S. Cl. ...................................... 351/209; 351/206
(58) Field of Classification Search ................ 351/205, 351/209, 210, 221, 246
See application file for complete search history.

(56) References Cited

U.S. PATENT DOCUMENTS

2004/0174496 A1* 9/2004 Ji et al. ....................... 351/209
2005/0175218 A1* 8/2005 Vertegaal et al. ........... 382/103

FOREIGN PATENT DOCUMENTS

JP 8-297019 11/1996

OTHER PUBLICATIONS

J.Y., Kaminski et al: "Three-Dimensional Face Orientation and Gaze Detection from a single image." Online! Aug. 4, 2004. Bar-Ilan University, XP002336128 Retrieved from the Internet: URL:Http://ariv.org/PS_cache/cs/pdf/0408/0408012.pdf. *the whole document*.
Ohno T et al: "FreeGaze: a gaze tracking system for everyday gaze interaction". Proceedings ETRA 2002. Eye Tracking Research and Applications Symposium ACM New York, NY, USA, 2002, pp. 125-132, XP002336136, ISBN: 1-58113-467-3, *paragraph'03. 2!—paragraph '3.2.1!; figure 8*.

(Continued)

*Primary Examiner*—Huy Mai
(74) *Attorney, Agent, or Firm*—Rankin, Hill, Porter & Clark LLP

(57) ABSTRACT

A line-of-sight detection method in an imaging system which includes a camera for photographing a face and right and left eyes and a light source for irradiating the right and left eyes with infrared rays, said line-of-sight detection method comprising:
  obtaining a center point of a pupil of at least one of the right and left eyes;
  obtaining a center point of a cornea spherical surface of said at least one of the right and left eyes; and
  obtaining a direction of a vector headed from said center point of said cornea spherical surface to said center point of said pupil,
  wherein a data based on a morphological information is used in obtaining said center point of said pupil.

4 Claims, 3 Drawing Sheets

OTHER PUBLICATIONS

Gee A et al: "Determining the gaze of faces in images", Image and Vision Computing UK, vol. 12, No. 10, Dec. 1994, pp. 639-647, XP002336137, ISSN: 0262-8856. *the whole document*.

"An Eyeball-Model-Based Eye Tracking Method", Eighth Image Sensing Symposium, pp. 307-312, 2002. (discussed on p. 2 of spec.).

An Eye Trasking System Based on Eye Ball Model -Toward Realization of Gaze Controlled Input Device-, Information Processing Research Report 2001-HI-93, pp. 47-54, 2001. (Discussed on p. 2 of spec.).

"Anthropometry of the Head and Face", by L.G. Farkas, Lippincott Williams & Wilkins, p. 272, 275, 288-289, 341-343, and 350, 1994.

* cited by examiner

LINE-OF-SIGHT DETECTION METHOD AND APPARATUS THEREFOR

This application claims foreign priority based on Japanese Patent application No. 2004-71256, filed Mar. 12, 2004, the contents of which is incorporated herein by reference in its entirety.

BACKGROUND OF THE INVENTION

1. Field of the Invention

The present invention relates to a line-of-sight detection technique used for an input device of a computer or for an auxiliary driving device when driving a vehicle.

2. Description of the Related Art

A line-of-sight detection technique has been studied as an input device of a computer for handicapped people who can not freely use their hands or fingers. The line-of-sight detection technique is also used as an auxiliary driving device of vehicles by monitoring the line of sight of a driver who is driving a vehicle. However, some line-of-sight detection apparatuses of the related arts require a user to wear a specific equipment, and since these techniques place restrictions on a movement of a user, their usability is unsatisfactory. In order to solve this problem, a technique of detecting the line of sight by using an eyeball model has been developed.

When an eyeball model is used, it becomes significant that an accurate distance from the position whereat a camera is located to the face of a user is obtained correctly by a simple method. For example, an apparatus disclosed in JP-A-8-297019 (line-of-sight measuring apparatus for vehicles) is an apparatus that detects the line of sight of a driver, and uses a distance sensor as a device that obtains the distance from the position whereat a camera is located to the face of the driver. As a distance sensor, an ultrasonic sensor or the like is used. However, when the ultrasonic sensor is used, the entire apparatus becomes complicated, while the detection accuracy would be reduced when a simpler sensor is used, and the apparatus would become too expensive when high accuracy is provided.

A technique of detecting the line of sight by using an eyeball model is also described in "An eye tracking system based on eyeball model", Information Processing Research Report 2001-HI-93, pp. 47-54, 2001, and "An eyeball-model-based eye tracking method", Eighth Image Sensing Symposium, pp. 307-312, 2002. In the apparatus described in these documents, near-infrared ray is irradiated to a cornea in the eye from a point light source, and obtains the distance from a camera (or the point light source) to the face in order to obtain coordinates of a reflected image (called as a Purkinje image). A focus value when a focus is adjusted to a position whereat the size of the point light source (the size of the Purkinje image) is the smallest In an image obtained by the camera is employed to obtain the distance. However, it is difficult to adjust the focus so that the size of the Purkinje image becomes smallest in exactly, and accordingly, an accurate distance measurement can not be expected. Further, there might be some error in the detection of the line of sight using the obtained distance.

Calibration may also be employed as a method of obtaining the distance between a camera and an object in real space. According to this method, however, the measurement system would be complicated as a coordinate model of the three-dimensional coordinate system is required in real space for calibration.

SUMMARY OF THE INVENTION

It is therefore an object of the invention to provide a method and an apparatus that obtains the accurate distance between a camera and a face by a simple method so as to obtain direction of line of sight easily.

In this invention, the following configuration is employed to achieve the object. According to a first aspect of the invention, a line-of-sight detection method in an imaging system which includes a camera for photographing a face and right and left eyes and a light source for irradiating the right and left eyes with infrared rays, said line-of-sight detection method comprising:

obtaining a center point of a pupil of at least one of the right and left eyes;

obtaining a center point of a cornea spherical surface of said at least one of the right and left eyes; and obtaining a direction of a vector headed from said center point of said cornea spherical surface to said center point of said pupil, wherein a data based on a morphological information (that is an information morphologically well known) is used in obtaining said center point of said pupil.

According to a second aspect of the invention, for the line-of-sight detection method of the first aspect, the data based on said morphological information are on the basis of facts that (1) distances from right and left eyes to nose are equal, (2) a ratio of the distance between the right eye and the left eye and the distances from the right and left eyes to the nose is a constant value, and (3) the distance between the right eye and the left eye is constant.

According to a third aspect of the invention, for the line-of-sight detection method of the first aspect, a data based on the fact that a center radius of a cornea spherical surface of an eye is a constant value is used in addition to said data based on said morphological information in obtaining said center point of said cornea spherical surface.

According to a fourth aspect of the invention, for the line-of-sight detection method of the second aspect, a data based on the fact that a center radius of a cornea spherical surface of an eye is a constant value is used in addition to said data based on said morphological information in obtaining said center point of said cornea spherical surface.

According to a fifth aspect of the invention, a line-of-sight detection apparatus comprising:

a camera which photographs a face and right and left eyes;

a light source which irradiates the right and left eyes with infrared rays; and an arithmetic processing unit which obtains a direction of line of sight by calculation based on a data obtained by said camera and a data based on a morphological information (that is an information morphologically well known.)

According to a sixth aspect of the invention, for the line-of-sight detection apparatus of the fifth aspect, the data based on said morphological information are on the basis of facts that (1) distances from right and left eyes to nose are equal, (2) a ratio of the distance between the right eye and the left eye and the distances from the right and left eyes to the nose is a constant value, and (3) the distance between the right eye and the left eye is constant.

According to a seventh aspect of the invention, for the line-of-sight detection apparatus of the fifth aspect, a data based on the fact that a center radius of a cornea spherical surface of an eye is a constant value is used in addition to said data based on said morphological information in obtaining the direction of line of sight.

According to an eighth aspect of the invention, for the line-of-sight detection apparatus of the sixth aspect, a data based on the fact that a center radius of a cornea spherical surface of an eye is a constant value is used in addition to said data based on said morphological information in obtaining the direction of line of sight.

DESCRIPTION OF THE PREFERRED EMBODIMENTS

Figure 1A:
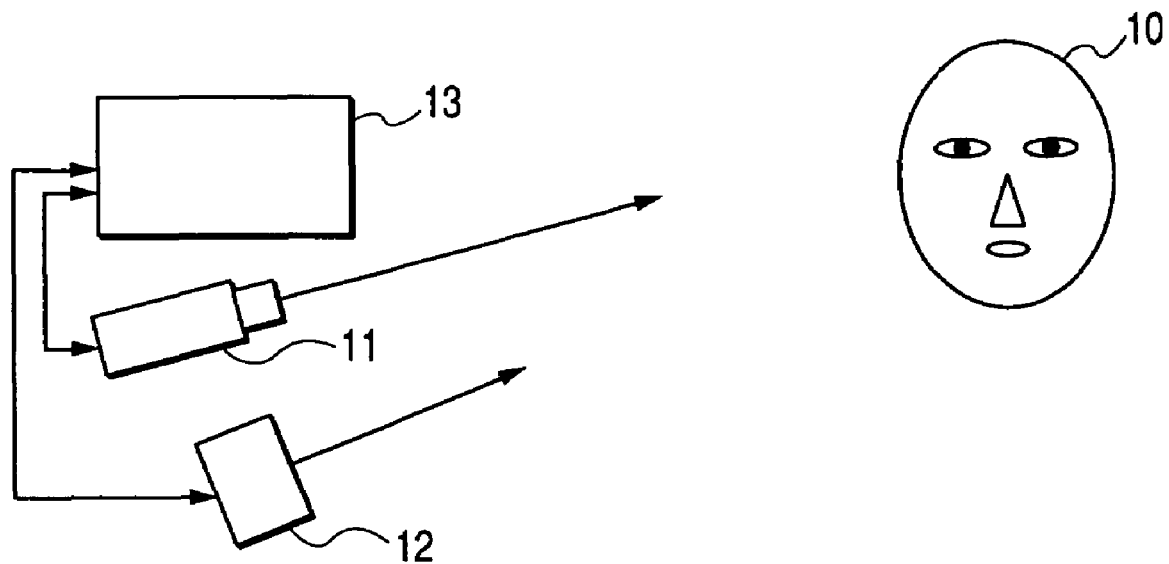
FIG. 1A is a diagram showing a system configuration according to one embodiment of the present invention.

One embodiment of the present invention will now be described while referring to the drawings.

Figure 1B:
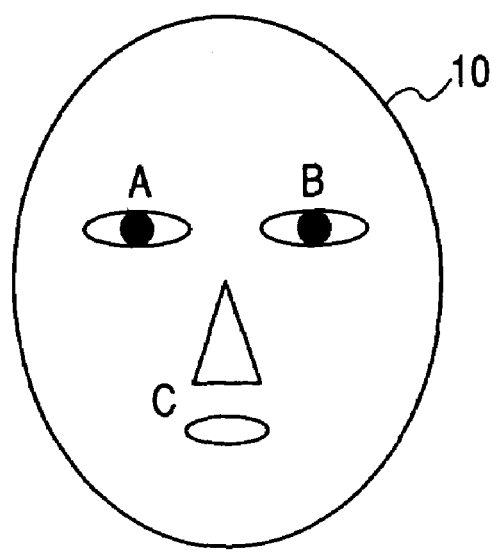
FIG. 1B is a diagram for explaining morphologically known data of a face.

FIG. 1A is a diagram showing a configuration of an apparatus according to the embodiment of the invention, and FIG. 1B is a diagram for explaining the morphological features of a face employed in this embodiment. In FIG. 1A, the apparatus comprises: a camera 11 that photographs a target object such as a face (or eyes) 10 of a human being; a diode 12 that emits infrared rays; and a computer 13 that performs various calculations based on image data acquired from a photographed image and controls the camera 11 and the diode 12. The positional coordinates and the directional angle of the camera 11, and the positional coordinates and the directional angle of the infrared ray emitting diode 12 are given. Further, the focal distance (f) and the camera parameter (K) of the camera 11 are also given.

As shown in FIG. 1B, the face 10 of a human being has a right eye A, a left eye B, a nose C and a mouth. When the coordinate of the right eye A is $(A_x, A_y, A_z)$, the coordinate of the left eye B is $(B_x, B_y, B_z)$ and the coordinate of the nose C is $(C_x, C_y, C_z)$, it is morphologically known that the following relations are formed, as described in "Anthropometry of the Head and Face", by L. G. Farkas, Lippincott Williams & Wilkins, pg. 272,275,288-289,341-343,349 and 350, 1994, for example.

$$d(A, C) = d(B, C) \quad (1)$$

$$r = d(A, B)/d(A, C) = 1.0833 \quad (2)$$

$$d(A, B) = 6.5 \text{ (cm)} \quad (3)$$

$$\text{radius of cornea} = 7.7 \text{(mm)} \quad (4)$$

In the relationship above, "d(*, *)" denotes a distance between two points, and "/" denotes a division.

Figure 2:
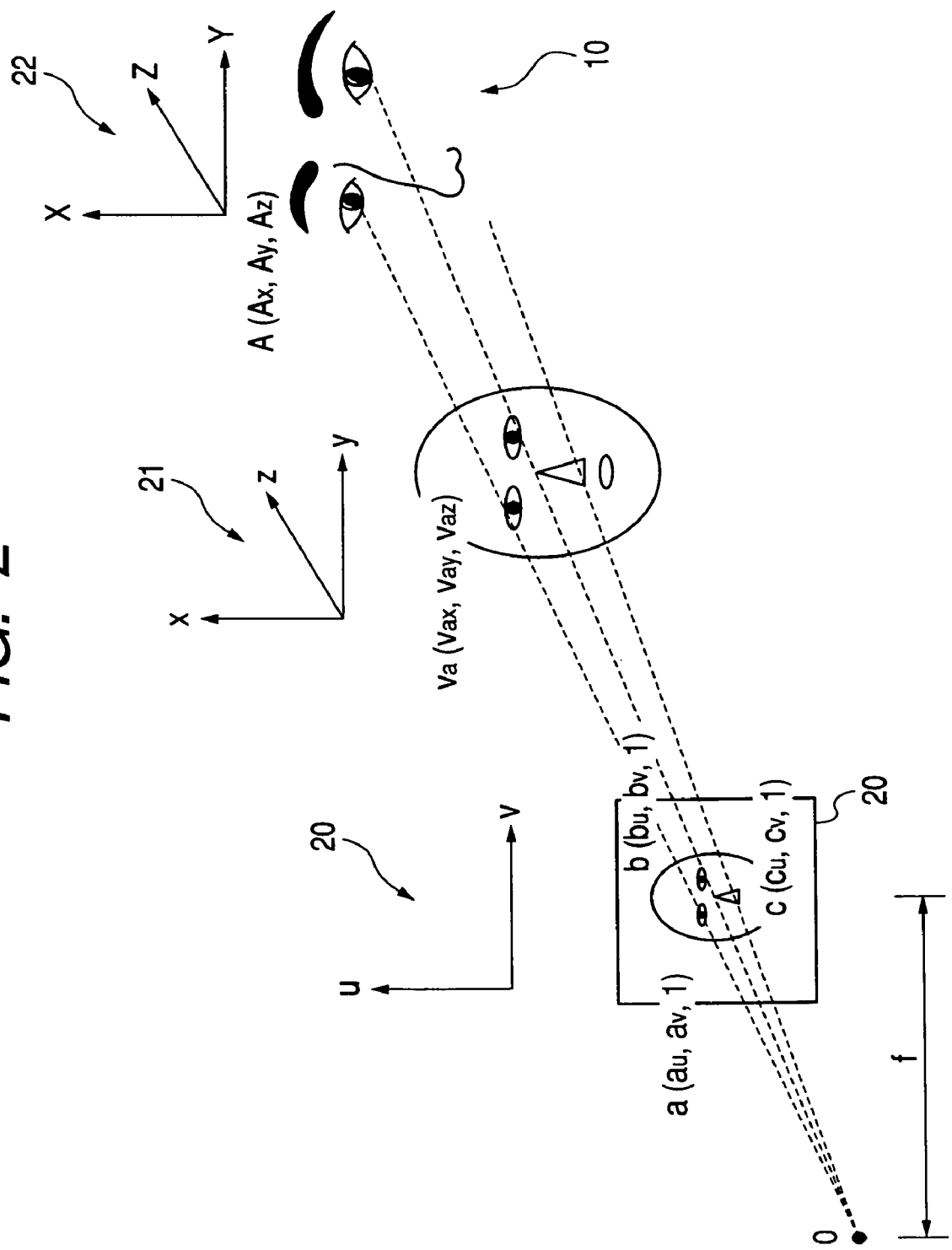
FIG. 2 is a diagram showing the relationship of individual coordinate systems.

FIG. 2 shows the positions of individual coordinate systems. In FIG. 2, the origin O is assumed to be the center of the lens of the camera 11. A two-dimensional coordinate system 20 (u, v) is a coordinate system of a photographed image plane, and is a planar coordinate system located at a distance of the focal length f (f=1) of the camera 11 from the origin O. A three-dimensional coordinate system (x, y, z) 21 is a standard coordinate system that is provided in order to reduce rounding errors in numerical calculations. The coordinate system 21 is provided so as to convert scales of the individual axes used in a world coordinate system (X, Y, Z) 22 and obtain individual data uniformalized in size. That is, since the results of numerical calculations become less reliable when numerical values are varied depending on the units employed in each coordinate in the world coordinate system 22, it is necessary to uniformalize size of data.

Assume that the coordinate of the right eye in the coordinate system 20 is $a(a_u, a_v, 1)$, the coordinate of the left eye is $b(b_u, b_v, 1)$ and the coordinate of the nose is $c(c_u, c_v, 1)$; that the coordinate of the right eye in the coordinate system 21 is $v_a(v_{ax}, v_{ay}, v_{az})$, the coordinate of the left eye is $v_b(v_{bx}, v_{by}, v_{bz})$ and the coordinate of the nose is $v_c(v_{cx}, v_{cy}, v_{cz})$; and that the coordinate of the right eye in the world coordinate system 22 is $A(A_x, A_y, A_z)$, the coordinate of the left eye is $B(B_x, B_y, B_z)$ and the coordinate of the nose is $C(C_x, C_y, C_z)$.

An arbitrary point p=p(u, v, 1) in the coordinate system 20 and a corresponding point v=v(x, y, z) in the coordinate system 21 can be represented as p=Kv by using a camera parameter matrix (K). The point p in the coordinate system 20 of a photographed image plane is given by reading the point on the photographed image. As an inverse matrix $(K^{-1})$ for the camera parameter matrix (K) exits, the corresponding point v of the point p is also given. That is, the points $v_a$, $v_b$ and $v_c$ can be obtained by the following Expression 1. It should be noted that a superscript "T" represents transposition in Expression 1.

$$(V_{ax}, V_{ay}, V_{az})^T = K^{-1} * (a_u, a_v, 1)^T$$

$$(V_{bx}, V_{by}, V_{bz})^T = K^{-1} * (b_u, b_v, 1)^T$$

$$(V_{cx}, V_{cy}, V_{cz})^T = K^{-1} * (c_u, c_v, 1)^T \quad \text{[Expression 1]}$$

Further, as shown in FIG. 2, since a corresponding point M=M(X, Y, Z) in the world coordinate system 22 of the point v in the coordinate system 21 is located on a line extended from the origin O, the following Expression 2 is formed when the scale parameter is ($\lambda$, $\mu$, $\tau$).

$$(A_x, A_y, A_z)^T = \lambda * (V_{ax}, Y_{ay}, V_{az})$$

$$(B_x, B_y, B_z)^T = \mu * (V_{bx}, Y_{by}, V_{bz})$$

$$(C_x, C_y, C_z)^T = \tau * (V_{cx}, Y_{cy}, V_{cz}) \quad \text{[Expression 2]}$$

When Expressions 1 and 2 are substituted for the described relations (1) to (3), unknown scale parameter ($\lambda$, $\mu$, $\tau$) can be obtained by numerical calculation, and the right eye position A, the left eye position B and the nose position C in the world coordinate system 22 can be determined. Therefore, a normal vector N of the face is obtained from Expression 2. Also, the distances from the origin O to the points A, B and C are obtained.

Figure 3:
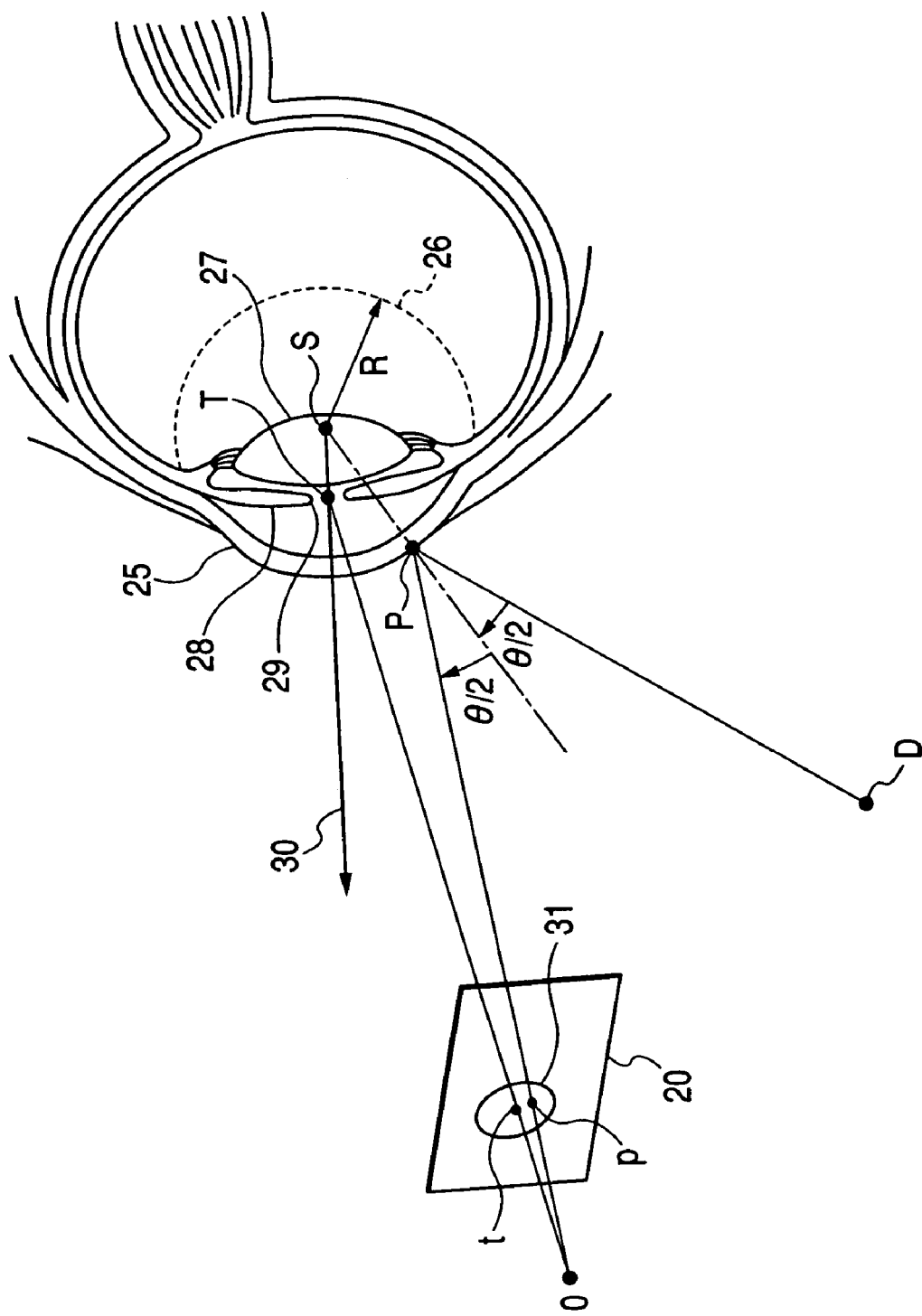
FIG. 3 is a diagram showing a relationship between an eyeball model and a direction of line of sight.

FIG. 3 is a diagram showing a relationship between the structure of an eye and the direction of the line of sight. In FIG. 3, a cornea 25 is located on the outer surface of the eyeball, and constitutes apart of a cornea spherical surface 26 that is indicated by a dotted line. The cornea spherical surface 26 is a virtual shell having a center S and a radius R. As described above about the morphological features of the face, the radius R is defined as R=7.7 mm. Furthermore, an iris 28 that adjusts the amount of incident light is positioned on the front side of a lens 27, and a part which can be seen from an opening of the iris 28 is a pupil 29. An arrow headed a straight line 30 that connects the center $S(S_x, S_y, S_z)$ of the cornea spherical surface 26 and a center $T(T_x, T_y, T_z)$ of the pupil 29 represents the direction of line of sight.

In a photographed image 20, a circle 31 represents an image of the pupil 29, and a center point t of the image represents the center T of the pupil 29. Since the coordinate $(t_u, t_v)$ of the center point t can be read and obtained from the photographed image 20, the coordinate $(T_x, T_y, T_z)$ of the center T of the pupil 29 can be determined from the following relations (5) and (6) based on the coordinate of the center point t. It should be noted that a distance (f) denotes a focal distance of the camera 11, and symbol "·" denotes a scalar product.

(5) $T_z$ is substantially equal to a distance d(OA) between the origin O and the eye A (or the eye B). That is, $T_z$=d(OA).

$$T_x=(T_z/f)\cdot t_u,\ T_y=(T_z/f)\cdot t_v \qquad (6)$$

The center $S(S_x, S_y, S_z)$ of the cornea spherical surface 26 is obtained as follows. Infrared ray emitted from an infrared ray emitting point D is reflected at a luminescent spot P on the cornea 25, and enters the origin O. The coordinate $(D_x, D_y, D_z)$ of the infrared ray emitting point D is given, a dista d(OP) between the origin O and the luminescent spot P is d(OP)=d(OA)=$T_z$, and the incident angle and the reflection angle are equal by (θ/2). Therefore, both the coordinate $(P_x, P_y, P_z)$ of the luminescent spot P and the normal vector at the luminescent spot P can be determined.

However, when the infrared ray emitting point D is located considerably close to the camera 11, the coordinate $(P_x, P_y, P_z)$ od the luminescent spot P can be obtained based on the point $p(p_u, p_v)$ on the photographed image, in a same method as that used to obtain the center T of the pupil 29. Further, the center S of the cornea spherical surface 26 may be defined to be on the line that passes the points D and P. When the vector from the infrared ray emitting point D to the luminescent spot P is defined as V(DP), the center $S(S_x, S_y, S_z)$ of the cornea spherical surface 26 can be obtained from the following relation (7).

$$S(S_x, S_y, S_z)=P(P_x, P_y, P_z)+R\cdot(V(DP)/d(DP))$$

In the above relation (7), S and P denote vectors from the origin, R denotes the radius of the cornea spherical surface 26 which is R=7.7 mm, and "d" denotes a distance (norm).

The relation (7) includes three simultaneous equations, and since $(S_x, S_y, S_z)$ can be obtained by the relation (7) while the coordinate $(T_x, T_y, T_y)$ of the center T of the pupil 29 can be obtained as described above, direction from the point S to the center T, i.e., the direction of the line of sight can be determined.

According to the method described above, the distance from the camera to the face can be accurately obtained, and when the infrared ray emitting point D is located considerably close to the camera 11, both the center S of the cornea spherical surface 26 and the center T of the pupil 29 can be obtained with high accuracy. Therefore, according to this method, direction of line of sight can be obtained with high accuracy by a simple system.

The present invention provides effects such that a direction of line of sight can be detected accurately using a simple apparatus.

It will be apparent to those skilled in the art that various modifications and variations can be made to the described preferred embodiments of the present invention without departing from the spirit or scope of the invention. Thus, it is intended that the present invention cover all modifications and variations of this invention consistent with the scope of the appended claims and their equivalents.

What is claimed is:

1. A line-of-sight detection method in an imaging system which includes a camera for photographing a face and right and left eyes and a light source for irradiating the right and left eyes with infrared rays, said line-of-sight detection method comprising:
    obtaining a center point of a pupil of at least one of the right and left eyes;
    obtaining a center point of a cornea spherical surface of said at least one of the right and left eyes; and
    obtaining a direction of a vector headed from said center point of said cornea spherical surface to said center point of said pupil,
    wherein a data based on a morphological information is used in obtaining said center point of said pupil, and wherein the data based on said morphological information are on the basis of facts that (1) distances from right and left eyes to nose are equal, (2) a ratio of the distance between the right eye and the left eye and the distances from the right and left eyes to the nose is a constant value, and (3) the distance between the right eye and the left eye is constant.

2. The line-of-sight detection method according to claim 1, wherein a data based on the fact that a center radius of a cornea spherical surface of an eye is a constant value is used in addition to said data based on said morphological information in obtaining said center point of said cornea spherical surface.

3. A line-of-sight detection apparatus comprising:
    a camera which photographs a face and right and left eyes;
    a light source which irradiates the right and left eves with infrared rays; and
    an arithmetic processing unit which obtains a direction of line of sight by calculation based on a data obtained by said camera and a data based on a morphological information, and wherein the data based on said morphological information are on the basis of facts that (1) distances from right and left eyes to nose are equal, (2) a ratio of the distance between the right eye and the left eye and the distances from the right and left eyes to the nose is a constant value, and (3) the distance between the right eye and the left eye is constant.

4. The line-of-sight detection apparatus according to claim 3, wherein a data based on the fact that a center radius of a cornea spherical surface of an eye is a constant value is used in addition to said data based on said morphological information in obtaining the direction of line of sight.

\* \* \* \* \*